US012702726B2

(12) United States Patent
Chen et al.

(10) Patent No.: US 12,702,726 B2
(45) Date of Patent: Aug. 11, 2026

(54) MULTI-BAND LED DISINFECTION SYSTEM AND MULTI-BAND LED DISINFECTION LAMP

(71) Applicants: SHANGHAI SANSI ELECTRONIC ENGINEERING CO. LTD., Shanghai (CN); SHANGHAI SANSI TECHNOLOGY CO. LTD., Shanghai (CN); JIASHAN SANSI OPTOELECTRONIC TECHNOLOGY CO. LTD., Zhejiang (CN); PUJIANG SANSI OPTOELECTRONIC TECHNOLOGY CO. LTD., Jinhua City (CN)

(72) Inventors: Bishou Chen, Shanghai (CN); Ming Chen, Shanghai (CN); Shan Li, Shanghai (CN); Xiaoliang He, Shanghai (CN)

(73) Assignees: SHANGHAI SANSI ELECTRONIC ENGINEERING CO. LTD., Shanghai (CN); SHANGHAI SANSI TECHNOLOGY CO. LTD., Shanghai (CN); JIASHAN SANSI OPTOELECTRONIC TECHNOLOGY CO. LTD., Zhejiang (CN); PUJIANG SANSI OPTOELECTRONIC TECHNOLOGY CO. LTD., Zhejiang (CN)

( * ) Notice: Subject to any disclaimer, the term of this patent is extended or adjusted under 35 U.S.C. 154(b) by 388 days.

(21) Appl. No.: 18/287,640

(22) PCT Filed: May 26, 2021

(86) PCT No.: PCT/CN2021/096097
§ 371 (c)(1),
(2) Date: Oct. 19, 2023

(87) PCT Pub. No.: WO2022/222223
PCT Pub. Date: Oct. 27, 2022

(65) Prior Publication Data

US 2024/0189471 A1 Jun. 13, 2024

(30) Foreign Application Priority Data

Apr. 20, 2021 (CN) ......................... 202110425265.6
Apr. 20, 2021 (CN) ......................... 202120816181.0

(51) Int. Cl.
*A61L 2/24* (2006.01)
*A61L 2/084* (2026.01)
(Continued)

(52) U.S. Cl.
CPC ................. *A61L 2/24* (2013.01); *A61L 2/084* (2013.01); *A61L 2/10* (2013.01); *F21V 29/70* (2015.01);
(Continued)

(58) Field of Classification Search
CPC ... A61L 2/24; A61L 2/084; A61L 2/10; A61L 2202/11; A61L 2202/14; A61L 2202/16;
(Continued)

(56) References Cited

U.S. PATENT DOCUMENTS 6,211,626 B1 * 4/2001 Lys .......................... G09G 3/32
315/324
6,292,901 B1 * 9/2001 Lys ...................... A61N 5/0618
713/300
(Continued)

FOREIGN PATENT DOCUMENTS

CN 203363755 U * 12/2013
CN 106669288 A 5/2017
(Continued)

*Primary Examiner* — David A Vanore

(74) *Attorney, Agent, or Firm* — IPRTOP LLC

(57) ABSTRACT

A multi-band LED disinfection system and a multi-band LED disinfection lamp are provided. The multi-band LED disinfection system comprises a multi-band LED disinfection device; and a control terminal, which is connected to and controls the multi-band LED disinfection device. The control terminal sends a wavelength band control command to the multi-band LED disinfection device according to a disinfection target, and the multi-band LED disinfection device drives LED beads of corresponding wavelength bands. Different wavelength bands of ultraviolet light can be provided to achieve the disinfection of various germs, which leads to better sterilization and disinfection effects. A control module can be used to switch between disinfection of a certain wavelength band and disinfection of superposed wavelength bands. The present disclosure has both a sterilization-and-disinfection function, and an illumination-and-warning function, and non-related personnel can be prevented through the illumination-and-warning function from approaching the lamp during the sterilization and disinfection process.

10 Claims, 1 Drawing Sheet

(51) Int. Cl.

| | |
|---|---|
| ***A61L 2/10*** | (2026.01) |
| ***F21V 29/70*** | (2015.01) |
| ***F21Y 113/00*** | (2016.01) |
| ***F21Y 113/13*** | (2016.01) |
| ***F21Y 115/10*** | (2016.01) |
| ***H05B 45/30*** | (2020.01) |

(52) U.S. Cl.
CPC .......... *H05B 45/30* (2020.01); *A61L 2202/11* (2013.01); *A61L 2202/14* (2013.01); *F21Y 2113/13* (2016.08); *F21Y 2113/30* (2023.05); *F21Y 2115/10* (2016.08)

(58) Field of Classification Search
CPC ........ A61L 2202/25; A61L 9/20; F21V 29/70; H05B 45/30; H05B 45/20; F21Y 2113/13; F21Y 2113/30; F21Y 2115/10
See application file for complete search history.

(56) References Cited

U.S. PATENT DOCUMENTS

| | | | | |
|---|---|---|---|---|
| 6,459,919 | B1 * | 10/2002 | Lys | H05B 45/20 600/407 |
| 6,528,954 | B1 * | 3/2003 | Lys | H05B 45/46 315/158 |
| 7,227,750 | B2 * | 6/2007 | Chen | H10H 20/8582 362/373 |
| D714,488 | S * | 9/2014 | Chen | D26/123 |
| 10,094,548 | B2 * | 10/2018 | Draper | F21V 29/70 |
| 11,187,387 | B1 * | 11/2021 | Yan | F21K 9/232 |
| 11,242,958 | B2 * | 2/2022 | Halliwell | F21V 19/006 |
| 11,248,753 | B1 * | 2/2022 | Li | F21K 9/232 |
| 11,455,884 | B2 * | 9/2022 | Bosua | F21V 23/0435 |
| 2006/0001384 | A1 * | 1/2006 | Tain | H05B 45/20 315/246 |
| 2008/0265179 | A1 * | 10/2008 | Havens | A61L 2/10 250/492.1 |
| 2012/0307491 | A1 * | 12/2012 | Chen | F21V 23/06 362/249.02 |
| 2014/0264070 | A1 * | 9/2014 | Bettles | A61L 2/10 250/435 |
| 2015/0036863 | A1 * | 2/2015 | Wen | H04R 1/028 381/386 |
| 2015/0167937 | A1 * | 6/2015 | Casper | F21V 15/012 362/373 |
| 2015/0300579 | A1 * | 10/2015 | Wang | F21V 29/717 362/249.02 |
| 2016/0128526 | A1 * | 5/2016 | Dobrinsky | A47K 13/302 4/233 |
| 2016/0227636 | A1 * | 8/2016 | Sun | H05B 45/30 |
| 2016/0271280 | A1 * | 9/2016 | Liao | G06F 3/0393 |
| 2016/0329624 | A1 * | 11/2016 | Chen | H05B 47/19 |
| 2016/0341368 | A1 * | 11/2016 | ChEN | F21K 9/238 |
| 2016/0363339 | A1 * | 12/2016 | Blackley | A61L 9/14 |
| 2017/0348445 | A1 | 12/2017 | Bogdanovich | |
| 2018/0117194 | A1 * | 5/2018 | Dobrinsky | A61L 2/10 |
| 2019/0128482 | A1 * | 5/2019 | Jiang | H05B 45/345 |
| 2019/0336629 | A1 * | 11/2019 | Dobrinsky | A61L 2/10 |
| 2020/0101183 | A1 | 4/2020 | Dijkstra et al. | |
| 2020/0268921 | A1 * | 8/2020 | Lepine | A61L 2/08 |
| 2020/0363052 | A1 * | 11/2020 | Li | F21K 9/20 |
| 2020/0398077 | A1 * | 12/2020 | Ball | A61N 5/0624 |
| 2021/0215319 | A1 * | 7/2021 | Raring | H01S 5/0225 |
| 2021/0275702 | A1 * | 9/2021 | Parkansky | F21V 14/04 |
| 2021/0352792 | A1 * | 11/2021 | Bogart | F21K 9/232 |
| 2021/0369905 | A1 * | 12/2021 | Bosua | F21V 23/045 |
| 2022/0065434 | A1 * | 3/2022 | He | F21V 17/16 |
| 2022/0290851 | A1 * | 9/2022 | Zhang | A61L 9/20 |
| 2022/0418061 | A1 * | 12/2022 | Chen | H05B 45/18 |
| 2023/0007892 | A1 * | 1/2023 | Chen | F21V 29/83 |
| 2023/0126492 | A1 * | 4/2023 | Chen | H05B 47/115 315/153 |
| 2023/0248862 | A1 * | 8/2023 | Benner | A61L 2/10 422/24 |

FOREIGN PATENT DOCUMENTS

| | | | | | |
|---|---|---|---|---|---|
| CN | 108386737 | A | * | 8/2018 | F21K 9/232 |
| CN | 109640443 | A | | 4/2019 | |
| CN | 111120977 | A | | 5/2020 | |
| CN | 111388724 | A | | 7/2020 | |
| CN | 111561673 | A | | 8/2020 | |
| CN | 219606987 | U | * | 8/2023 | |
| DE | 102013110257 | A1 | * | 3/2014 | H05B 45/00 |
| KR | 100990332 | B1 | * | 10/2010 | F21V 23/02 |
| WO | WO-0034709 | A1 | * | 6/2000 | F21V 29/83 |
| WO | WO-2011160452 | A1 | * | 12/2011 | F21K 9/232 |

* cited by examiner

MULTI-BAND LED DISINFECTION SYSTEM AND MULTI-BAND LED DISINFECTION LAMP

CROSS REFERENCE TO RELATED PATENT APPLICATION

The present application is the US national stage of PCT/CN2021/096097 filed on 2021 May 26, which claims the priorities of the Chinese patent application No. 202110425265.6 filed on 2021 Apr. 20 and Chinese patent application No. 202120816181.0 filed on 2021 Apr. 20, which applications are incorporated herein by reference.

FIELD OF TECHNOLOGY

The present disclosure relates to the technical field of ultraviolet sterilization and illumination, in particular, to a multi-band LED disinfection system and a multi-band LED disinfection lamp.

BACKGROUND

Ultraviolet sterilization and disinfection is a common method for killing germs. Ultraviolet rays can directly damage the genetic material of germs, causing them to die or become unable to reproduce. However, different germs require ultraviolet rays of different wavelength bands for effective sterilization and disinfection. Unfortunately, most ultraviolet sterilization lamps on the market only emit ultraviolet rays of a single wavelength band, making it difficult to meet modern sterilization needs. Therefore, there is an urgent need in this field for a multi-band sterilization and disinfection device that can be adjusted according to needs.

SUMMARY

In view of the above-mentioned shortcomings of existing technologies, the present disclosure aims to solve the technical problem that the wavelength band of ultraviolet light provided by the existing ultraviolet disinfection lamps is mostly single and cannot be adjusted, so as to achieve effective sterilization for different types of germs.

A first aspect of the present disclosure provides a multi-band LED disinfection system, comprising: a multi-band LED disinfection device; and a control terminal, which is connected to and controls the multi-band LED disinfection device; wherein the control terminal sends a wavelength band control command to the multi-band LED disinfection device according to a disinfection target, and the multi-band LED disinfection device drives LED beads of corresponding wavelength bands.

In some embodiments of the first aspect of the present disclosure, the multi-band LED disinfection device comprises a smart module, communicatively connected to the control terminal, wherein the smart module receives the wavelength band control command and converts the wavelength band control command into a corresponding LED driving signal; an LED bead unit, comprising disinfection LED beads and illumination LED beads; and a power driving unit, connected with the smart module and the LED bead unit, wherein the power driving unit receives the LED driving signal and drives the LED beads of the corresponding wavelength bands.

In some embodiments of the first aspect of the present disclosure, the control terminal sends the wavelength band control command to the smart module according to the disinfection target, the smart module converts the wavelength band control command into the LED driving signal, and the power driving unit drives the LED bead unit based on the LED driving signal, wherein the power driving unit drives the disinfection LED beads to emit light of disinfecting wavelength bands and drives the illumination LED beads to emit illumination light and/or warning light.

In some embodiments of the first aspect of the present disclosure, the disinfection LED beads comprise UVA LED beads, UVB LED beads, and UVC LED beads, and the illumination LED beads comprise one or more of white-light LED beads, red-light LED beads, green-light LED beads, and blue-light LED beads.

A second aspect of the present disclosure provides a multi-band LED disinfection lamp, comprising: a light source module, comprising a heat dissipation substrate and multiple groups of LED beads disposed on the heat dissipation substrate; a power module, comprising a smart control module and a power driving component connected with the smart control module, wherein the smart control module is used for receiving an LED driving command, wherein the power driving component is connected to and drives the LED beads, and the power driving component is used for supplying power to the light source module.

In some embodiments of the second aspect of the present disclosure, the multiple groups of LED beads comprise disinfection LED beads and illumination LED beads.

In some embodiments of the second aspect of the present disclosure, the disinfection LED beads comprise UVA LED beads, UVB LED beads, and UVC LED beads, and the illumination LED beads comprise one or more of white-light LED beads, red-light LED beads, green-light LED beads, and blue-light LED beads.

In some embodiments of the second aspect of the present disclosure, the UVA LED beads, the UVB LED beads, the UVC LED beads, and the illumination LED beads are respectively arranged in circles with different diameters so that the multiple groups of LED beads have a nested structure.

In some embodiments of the second aspect of the present disclosure, the heat dissipation substrate is a ceramic heat dissipation substrate, an adapter plate is welded on the ceramic heat dissipation substrate, and input lines of the power module are connected to the multiple groups of LED beads through the adapter plate.

In summary, the multi-band LED disinfection system and the multi-band LED disinfection lamp of the present disclosure have the following beneficial effects: different wavelength bands of ultraviolet light can be provided to achieve the disinfection of various germs, which leads to better sterilization and disinfection effects; a control module can be used to switch between disinfection of a certain wavelength band and disinfection of superposed wavelength bands. The present disclosure has both a sterilization-and-disinfection function, and an illumination-and-warning function, and non-related personnel can be prevented through the illumination-and-warning function from approaching the lamp during the sterilization and disinfection process. In contrast to traditional single-function disinfection lamps, the multi-band LED disinfection lamp of the present disclosure has multiple uses and can meet various disinfection needs, and has a more compact structure and occupies less space. In addition, the multi-band LED disinfection lamp has an indicator function, which improves the safety of ultraviolet disinfection.

DETAILED DESCRIPTION

Figure 1:
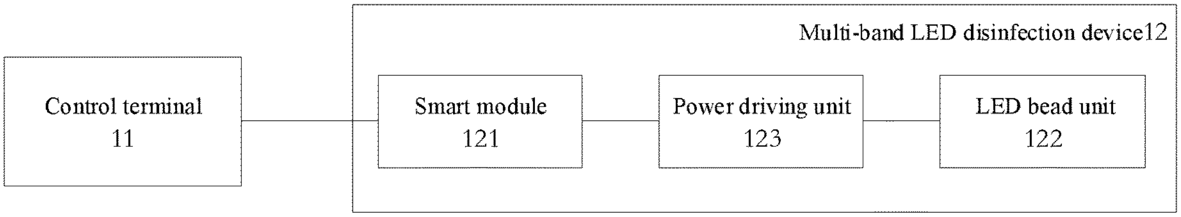
FIG. 1 shows a schematic structural diagram of a multi-band LED disinfection system in an embodiment of the present disclosure.

The embodiments of the present disclosure will be described below. Those skilled can easily understand disclosure advantages and effects of the present disclosure according to contents disclosed by the specification. The present disclosure can also be implemented or applied through other different exemplary embodiments. Various modifications or changes can also be made to all details in the specification based on different points of view and applications without departing from the spirit of the present disclosure. It should be noted that the following embodiments and the features of the following embodiments can be combined with each other if no conflict will result.

In the following description, the drawings describe several embodiments of the present disclosure. It should be understood that other embodiments can also be used to implement the present disclosure, and changes in mechanical composition, structure, electricity and operation can be made without departing from the spirit and scope of the present disclosure. The following detailed description should not be considered as restrictive. The terms used herein are only intended to describe specific embodiments and are not intended to restrict the present disclosure. Spatial terms, such as "up", "down", "left", "right", "below", "under", "beneath", "above", "over", etc., can be used herein to facilitate the description of the relationship between one element or feature and another element or feature shown in the figures.

In the present disclosure, unless otherwise expressly specified, terms such as "installation", "connection", "coupling", "fixing", and "holding" should be broadly understood. For example, when one element is referred to as being "connected to" another element, one element may be fixedly connected to or detachably connected to another element, may be mechanically connected to or electrically connected to another element, may be directly connected to another element, or may be indirectly connected to another element with another element interposed therebetween. These two elements may also communicate with each other internally. For those skilled in the art, the specific meanings of the above terms in the present disclosure can be understood based on specific situations.

As used herein, the singular forms "a", "an" and "said/the" are intended to include the plural forms, unless the context clearly points out differently. It should be further understood that the terms "include" and "comprise" indicate the existence of the described features, steps, operations, elements, components, items, categories, and/or groups, but do not exclude the existence, presence, or addition of one or more other features, steps, operations, elements, components, items, categories, and/or groups. As used herein, the terms "or" and "and/or" are inclusive, and are used to include any of the associated listed items and all combinations thereof. Thus, "A, B or C" or "A, B and/or C" means "any of the following: A; B; C; A and B; A and C; B and C; A, B and C". Exceptions to this definition apply only when combinations of elements, functions or operations are inherently paradoxical in some way.

The multi-band LED disinfection lamp of the present disclosure can emit different wavelength bands of ultraviolet, which can be adjusted by a control module. In addition, the multi-band LED disinfection lamp also comprises an illumination part capable of emitting visible light to achieve illumination or indication. In order to make the inventive purpose, technical solutions and beneficial technical effects of the present disclosure clearer, the present disclosure is described in further detail below through the following embodiments in conjunction with the accompanying drawings. It should be noted that the specific embodiments described herein are only illustrative, and are not intended to restrict the present disclosure.

FIG. 1 shows a schematic structural diagram of a multi-band LED disinfection system in an embodiment of the present disclosure. The multi-band LED disinfection system comprises a control terminal 11 and a multi-band LED disinfection device 12, and the control terminal 11 is connected to and controls the multi-band LED disinfection device 12. The control terminal 11 sends a wavelength band control command to the multi-band LED disinfection device 12 according to a disinfection target, and the multi-band LED disinfection device 12 drives LED beads of corresponding wavelength bands.

The control terminal 11 may be one of the following controllers: advanced RISC machines (ARM) controllers, field programmable gate array (FPGA) controllers, System on Chip (SoC) controllers, digital signal processing (DSP) controllers, microcontroller unit (MCU) controllers, etc. The control terminal 11 may also be one of the following computing equipment: desktop computers, laptops, tablets, smart phones, smart bracelets, smart watches, smart helmets, smart TVs, personal digital assistants (PDAs), etc. The control terminal 11 may further be a server, the server can be arranged on one or more physical servers according to various factors such as functions and loads, and the server can also be composed of distributed or centralized server clusters. The control terminal 11 may be an LED control panel. The multi-band LED disinfection device 12 comprises any LED products that utilize different wavelength bands of ultraviolet light to achieve sterilization and disinfection. These LED products can be LED lamps, LED displays, LED traffic lights, LED automotive lights, LED LCD screens, decorative LED lights, etc.

In addition, a communication connection may be directly established between the control terminal 11 and the multi-band LED disinfection device 12 based on short-range wireless communication methods. For example, the communication connection may be established through Bluetooth, infrared, WiFi, Zigbee, NB-IoT, or other wireless communication methods. The communication connection may also be established through a cloud server.

In one example, the multi-band LED disinfection device 12 comprises a smart module 121, an LED bead unit 122, and a power driving unit 123. Specifically, the smart module 121 is communicatively connected to the control terminal 11, and is used for receiving the wavelength band control command and converting the wavelength band control command into a corresponding LED driving signal. The power driving unit 123 is connected with the smart module 121 and the LED bead unit 122, and the power driving unit 123 is used for receiving the LED driving signal and driving the LED beads of the corresponding wavelength bands. By way of example, the control terminal 11 sends the wavelength band control command to the smart module 121 through a router, and the smart module 121 converts the wavelength band control command into a corresponding PWM signal after receiving the control command. The smart module 121 controls the LED beads by controlling a duty ratio of the PWM signal.

In some embodiments, the control terminal 11 sends the wavelength band control command to the smart module 121 according to the disinfection target, the smart module converts the wavelength band control command into the LED driving signal, and the power driving unit 123 drives the LED bead unit 122 based on the LED driving signal, wherein the power driving unit 123 drives the disinfection LED beads to emit light of disinfecting wavelength bands and drives the illumination LED beads to emit illumination light and/or warning light.

Specifically, the disinfection LED beads comprise UVA LED beads, UVB LED beads, and UVC LED beads, and the illumination LED beads comprise one or more of white-light LED beads, red-light LED beads, green-light LED beads, and blue-light LED beads.

It's important to note that UVA, UVB, and UVC LED beads are categorized based on the wavelength of their respective ultraviolet bands. The following is a breakdown of the different ultraviolet bands and the visible light band. UVA band is also known as long-wave black spot effect ultraviolet light and has a wavelength range of 400 nm to 320 nm. It has strong penetrating power and can pass through most transparent glass and plastic. Over 98% of the long-wave ultraviolet light in sunlight can penetrate the ozone layer and clouds to reach the Earth's surface. It can reach the dermis of the skin, damaging elastic fibers and collagen fibers, causing the skin to tan. UVA ultraviolet light with a wavelength of 360 nm meets the phototaxis response curve of insects, making it useful for insect lamps. UVB band is also known as medium-wave erythema effect ultraviolet light and has a wavelength range of 320 nm to 275 nm. It has medium penetrating power, with its shorter wavelengths being absorbed by transparent glass. Most of the medium-wave ultraviolet light in sunlight is absorbed by the ozone layer, with less than 2% reaching the Earth's surface. It is particularly strong in summer and afternoon. UVB ultraviolet light has an erythema effect on humans, promoting mineral metabolism in the body and the formation of vitamin D. Ultraviolet health lamps and plant growth lamps are made using special purple-transparent glass and fluorescent powder with a peak near 300 nm. UVC band is also known as short-wave sterilization ultraviolet light and has a wavelength range of 275 nm to 200 nm. It has the weakest penetrating power and cannot pass through most transparent glass and plastic. Almost all short-wave ultraviolet light in sunlight is completely absorbed by the ozone layer. Short-wave ultraviolet light is very harmful to humans, causing skin burns even with short-term exposure. Ultraviolet disinfection lamps emit UVC short-wave ultraviolet light. Visible light band is part of the electromagnetic spectrum that can be perceived by human eyes. Generally, electromagnetic waves with wavelengths between 780-400 nm can be perceived by human eyes, consisting of seven colors: red, orange, yellow, green, blue, indigo, and purple. Commonly used visible light lamps include incandescent lamps, halogen lamps, fluorescent lamps, energy-saving lamps, LED lamps, high-pressure sodium lamps, neon lamps, etc.

In some embodiments, the control terminal 11 sends a single-band control command to the smart module 121 according to the disinfection target, so that the LED beads of the corresponding wavelength bands are driven for performing illumination and disinfection. For example, the LED beads driven comprise the illumination LED beads and one of the disinfection LED beads. Specifically, the disinfection LED beads are used for disinfection and sterilization, and the illumination LED beads are used for indication or illumination, through which non-related personnel can be prevented from approaching the lamp during the sterilization and disinfection process. The visible light band is composed of various colors, comprising white light, red light, blue light, green light, and the like.

In some embodiments, the control terminal 11 sends a multi-band superposition command to the smart module 121 according to the disinfection target, and LED beads of different disinfecting wavelength bands are driven to achieve band superposition disinfection, i.e., disinfection of superposed wavelength bands. For example, the LED beads driven comprise the illumination LED beads and two of the disinfection LED beads (i.e., UVA+UVB, or UVA+UVC, or UVB+UVC). For another example, the LED beads driven comprise the illumination LED beads and three of the disinfection LED beads (i.e., UVA+UVB+UVC).

Figure 2:
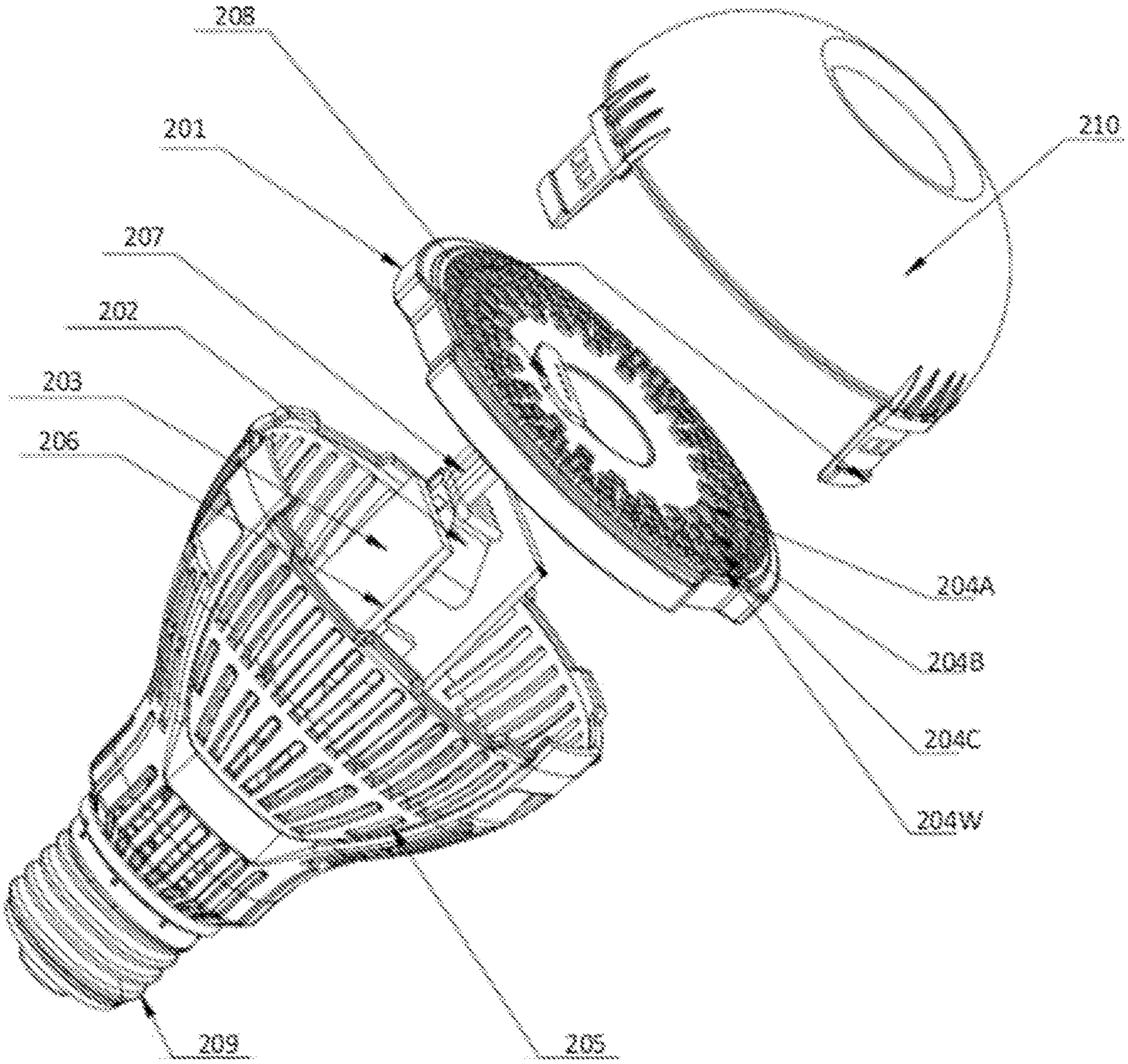
FIG. 2 shows a schematic structural diagram of a multi-band LED disinfection lamp in an embodiment of the present disclosure.

FIG. 2 shows a schematic structural diagram of a multi-band LED disinfection lamp in an embodiment of the present disclosure. It should be noted that the multi-band LED disinfection lamp of the present disclosure may be of various types. For example, the multi-band LED disinfection lamp may be indoor illumination lamps such as LED bulb lamps, fluorescent lamps, spotlights, table lamps, wall lamps, chandeliers, and ceiling lamps; the multi-band LED disinfection lamp may be commercial illumination lamps such as LED street lamps, landscape lamps, tunnel lamps, traffic lamps, and courtyard lamps; and the multi-band LED disinfection lamp may also be portable illumination lamps such as LED mining lamps and submarine lamps. For convenience of understanding, the specific structure of the multi-band LED disinfection lamp is described below by taking a bulb lamp as an example.

In one embodiment, the multi-band LED disinfection lamp comprises a light source module and a power module. The light source module comprises a heat dissipation substrate 201 and multiple groups of LED beads disposed on the heat dissipation substrate 201. The power module comprises a smart control module 202 and a power driving component 203 connected with the smart control module 202. The smart control module 202 is used for receiving an LED driving command. The power driving component 203 is connected to and drives the LED beads, and the power driving component 203 is used for supplying power to the light source module.

The multi-band LED disinfection lamp comprises a power chamber 205, and a power conversion board 206 is provided in the power chamber 205 to convert alternating current (AC) power into direct current (DC) power. The power driving component 203 is connected to input lines 207, and the input lines 207 is connected to an adapter plate 208, wherein the adapter plate 208 is disposed on the heat dissipation substrate 201. The smart control module 202 receives a wavelength band control command from external devices (such as a phone) and then converts the wavelength band control command into a corresponding PWM signal. The power driving component 203 is electrically connected to LED beads of corresponding wavelength bands through the input lines 207 and the adapter plate 208, so as to power and drive the LED beads.

In some embodiments, the multiple groups of LED beads comprise disinfection LED beads and illumination LED beads. The disinfection LED beads comprise UVA LED beads 204A, UVB LED beads 204B, and UVC LED beads 204C. The illumination LED beads comprise one or more of white-light LED beads, red-light LED beads, green-light LED beads, and blue-light LED beads. In FIG. 2, the white-light LED beads 204W are taken as an example.

Further, the UVA LED beads 204A, the UVB LED beads 204B, the UVC LED beads 204C, and the illumination LED beads (such as the white-light LED beads 204W) are respectively arranged in circles with different diameters, so that the multiple groups of LED beads have a nested structure. The above arrangement can not only prevent interference between each group of LED beads but also maximize the heat dissipation of each group of LED beads scattered on the heat dissipation substrate 201. It should be noted that the above-mentioned arrangement of the multiple groups of LED beads is only illustrative. Other arrangements (such as a staggered structure of LED beads) should also be considered as long as they can achieve the arrangement and layout of disinfection LED beads and illumination LED beads.

In some embodiments, the heat dissipation substrate 201 is a ceramic heat dissipation substrate. Compared with ordinary PCB substrates, ceramic heat dissipation substrates have lower thermal resistance and excellent thermal conductivity. They can package chips more compactly to improve power density and device reliability. In addition, ceramic heat dissipation substrates also have excellent thermal expansion coefficients, which leads to a reduced number of transition-layer molybdenum (Mo) sheets required, thus saving materials and reducing costs. Moreover, by using the ceramic heat dissipation substrates, the numbers of welding layers and cavities are reduced, the thermal resistance is reduced, and the yield is improved.

Furthermore, since it is difficult to directly perform wire welding on printed circuits of the ceramic heat dissipation substrates during production processes, the present disclosure applies the adapter plate 208, which is convenient for production and does not damage the ceramic heat dissipation substrates.

In the present disclosure, the bulb lamp further comprises a lamp base 209 and a bulb shell 210. The lamp base 209 is disposed at the bottom of the power chamber 205, and the bulb shell 210 covers the power chamber 205. A chamber space is formed between the bulb shell 210 and the power chamber 205, and various components of the bulb lamp are disposed in the chamber space.

In summary, the multi-band LED disinfection system and the multi-band LED disinfection lamp of the present disclosure have the following beneficial effects: different wavelength bands of ultraviolet light can be provided to achieve the disinfection of various germs, which leads to better sterilization and disinfection effects; a control module can be used to switch between disinfection of a certain wavelength band and disinfection of superposed wavelength bands. The present disclosure has both a sterilization-and-disinfection function, and an illumination-and-warning function, and non-related personnel can be prevented through the illumination-and-warning function from approaching the lamp during the sterilization and disinfection process. In contrast to traditional single-function disinfection lamps, the multi-band LED disinfection lamp of the present disclosure has multiple uses and can meet various disinfection needs, and has a more compact structure and occupies less space. In addition, the multi-band LED disinfection lamp has an indicator function, which improves the safety of ultraviolet disinfection. Therefore, the present disclosure effectively overcomes various shortcomings in the existing technology and has high industrial utilization value.

The above-mentioned embodiments are for exemplarily describing the principle and effects of the present disclosure instead of limiting the present disclosure. Those skilled in the art can make modifications or changes to the above-mentioned embodiments without going against the spirit and the range of the present disclosure. Therefore, all equivalent modifications or changes made by those who have common knowledge in the art without departing from the spirit and technical concept disclosed by the present disclosure shall be still covered by the scope of the present disclosure.

What is claimed is:

1. A multi-band LED disinfection system, comprising:
a multi-band LED disinfection device;
a processor-based controller, which is connected to and controls the multi-band LED disinfection device;
wherein the processor-based controller sends a wavelength band control command to the multi-band LED disinfection device according to a disinfection target, and the multi-band LED disinfection device drives LED beads of corresponding wavelength bands.

2. The multi-band LED disinfection system of claim 1, wherein the multi-band LED disinfection device comprises:
a microcontroller-based LED driver module, communicatively connected to the processor-based controller, wherein the microcontroller-based LED driver module receives the wavelength band control command and converts the wavelength band control command into a corresponding LED driving signal;
an LED bead unit, comprising disinfection LED beads and illumination LED beads; and
a power driving unit, connected with the microcontroller-based LED driver module and the LED bead unit, wherein the power driving unit receives the LED driving signal and drives the LED beads of the corresponding wavelength bands.

3. The multi-band LED disinfection system of claim 2, wherein the processor-based controller sends the wavelength band control command to the microcontroller-based LED driver module according to the disinfection target, the microcontroller-based LED driver module converts the wavelength band control command into the LED driving signal, and the power driving unit drives the LED bead unit based on the LED driving signal, wherein the power driving unit drives the disinfection LED beads to emit light of disinfecting wavelength bands and drives the illumination LED beads to emit illumination light and/or warning light.

4. The multi-band LED disinfection system of claim 3, wherein the processor-based controller sends a multi-band superposition command to the microcontroller-based LED driver module according to the disinfection target, and LED beads of different disinfecting wavelength bands are driven to achieve band superposition disinfection.

5. The multi-band LED disinfection system of claim 2, wherein the disinfection LED beads comprise UVA LED beads, UVB LED beads, and UVC LED beads, wherein the illumination LED beads comprise one or more of white-light LED beads, red-light LED beads, green-light LED beads, and blue-light LED beads.

6. A multi-band LED disinfection lamp, comprising:
a light source module, comprising a heat dissipation substrate and multiple groups of LED beads disposed on the heat dissipation substrate;
a power module, comprising a control circuit and a power driving component connected with the control circuit, wherein the control circuit is used for receiving an LED driving command, wherein the power driving component is connected to and drives the LED beads, and the power driving component is used for supplying power to the light source module.

7. The multi-band LED disinfection lamp of claim 6, wherein the multiple groups of LED beads comprise disinfection LED beads and illumination LED beads.

8. The multi-band LED disinfection lamp of claim 7, wherein the disinfection LED beads comprise UVA LED beads, UVB LED beads, and UVC LED beads, wherein the illumination LED beads comprise one or more of white-light LED beads, red-light LED beads, green-light LED beads, and blue-light LED beads.

9. The multi-band LED disinfection lamp of claim 8, wherein the UVA LED beads, the UVB LED beads, the UVC LED beads, and the illumination LED beads are respectively arranged in circles with different diameters so that the multiple groups of LED beads have a nested structure.

10. The multi-band LED disinfection lamp of claim 6, wherein the heat dissipation substrate is a ceramic heat dissipation substrate, an adapter plate is welded on the ceramic heat dissipation substrate, and input lines of the power module are connected to the multiple groups of LED beads through the adapter plate.

* * * * *